United States Patent
Koscielski et al.

(10) Patent No.: US 12,318,610 B1
(45) Date of Patent: Jun. 3, 2025

(54) GAIT TRAINER WITH NEUROMODULATION INTEGRATION

(71) Applicant: Enlighten Mobility, LLC, South Bend, IN (US)

(72) Inventors: Marissa Koscielski, Columbus, OH (US); Adrian Rodriguez, South Bend, IN (US); Leanne Tang, Evanston, IL (US)

(73) Assignee: ENLIGHTEN MOBILITY LLC, South Bend, IN (US)

( * ) Notice: Subject to any disclaimer, the term of this patent is extended or adjusted under 35 U.S.C. 154(b) by 732 days.

(21) Appl. No.: 17/074,036

(22) Filed: Oct. 19, 2020

Related U.S. Application Data

(60) Provisional application No. 62/916,863, filed on Oct. 18, 2019.

(51) Int. Cl.
  *A61N 1/36* (2006.01)
  *A61H 3/04* (2006.01)
  *A61N 1/04* (2006.01)

(52) U.S. Cl.
  CPC .......... *A61N 1/36003* (2013.01); *A61H 3/04* (2013.01); *A61N 1/0452* (2013.01); *A61N 1/0456* (2013.01); *A61N 1/0472* (2013.01); *A61N 1/36031* (2017.08); *A61H 2201/10* (2013.01); *A61H 2201/1642* (2013.01); *A61H 2201/5064* (2013.01); *A61H 2201/5071* (2013.01)

(58) Field of Classification Search
  CPC ............ A61N 1/36535; A61N 1/36542; A61N 1/36003
  See application file for complete search history.

(56) References Cited

U.S. PATENT DOCUMENTS

| | | | |
|---|---|---|---|
| 2,232,672 A | 2/1941 | Low | |
| 4,697,808 A * | 10/1987 | Larson | ................ A61H 1/0237 |
| | | | 482/901 |
| 5,092,329 A | 3/1992 | Graupe et al. | |
| 5,588,456 A | 12/1996 | Hart | |
| 5,662,560 A | 9/1997 | Svendsen | |
| 5,702,326 A | 12/1997 | Renteria | |
| 5,728,164 A | 3/1998 | Ferrari et al. | |
| 5,766,236 A | 6/1998 | Detty et al. | |
| 5,861,017 A | 1/1999 | Smith et al. | |

(Continued)

FOREIGN PATENT DOCUMENTS

| | | |
|---|---|---|
| AU | 686180 | 2/1998 |
| AU | 2002366287 | 6/2008 |

(Continued)

*Primary Examiner* — Alyssa M Alter
(74) *Attorney, Agent, or Firm* — Thompson Hine LLP

(57) ABSTRACT

A gait training device with neuromodulation integrated to stimulate the muscles of a patient who has a maladapted gait. In embodiments, the device includes a leg brace worn by the patient on their compromised limb. The leg brace is connected to a medical walker allowing the patient the support themselves while correcting their gait. In embodiments, the leg brace is connected via a gait trainer that directs the motion of the compromised limb to ensure proper biomechanical gait. One or more neuromodulators are attached or integrated into the leg brace and can deliver electrical impulses to the patient's compromised limb to facilitate gait correction.

9 Claims, 10 Drawing Sheets

(56) References Cited

U.S. PATENT DOCUMENTS

| | | |
|---|---|---|
| 6,029,090 A | 2/2000 | Herbst |
| 6,343,802 B1 | 2/2002 | Workman et al. |
| 6,507,757 B1 | 1/2003 | Swain et al. |
| 6,607,202 B1 | 8/2003 | Palmer |
| 6,645,126 B1 | 11/2003 | Martin et al. |
| 6,652,427 B2 | 11/2003 | Wroclawsky |
| 6,832,770 B1 | 12/2004 | Wright-Ott et al. |
| 7,150,722 B1 | 12/2006 | Tyrell |
| 7,422,550 B1 | 9/2008 | Pinero et al. |
| 8,209,022 B2 | 6/2012 | Dar et al. |
| 8,452,410 B2 | 5/2013 | Emborg et al. |
| 8,500,668 B2 | 8/2013 | Siegler et al. |
| 8,905,951 B2 | 12/2014 | Barriskill et al. |
| 9,114,257 B2 | 8/2015 | Helfer et al. |
| 9,314,622 B2 | 4/2016 | Embrey et al. |
| 9,370,680 B1 | 6/2016 | Macaulay et al. |
| 9,375,570 B2 | 6/2016 | Kiani et al. |
| 9,415,205 B2 | 8/2016 | Lasko et al. |
| 9,603,538 B2 | 3/2017 | Fisher et al. |
| 9,616,282 B2 | 4/2017 | Tholkes et al. |
| 9,649,243 B2 | 5/2017 | Johnson et al. |
| 9,662,526 B2 | 5/2017 | Agrawal et al. |
| 9,802,039 B2 | 10/2017 | Palermo et al. |
| 10,076,656 B2 | 9/2018 | Dar et al. |
| 10,376,734 B1 | 8/2019 | Razon |
| 10,406,059 B2 | 9/2019 | Agrawal et al. |
| 10,870,198 B1 | 12/2020 | Asbeck et al. |
| 2002/0010056 A1 | 1/2002 | Borsheim |
| 2003/0093021 A1 | 5/2003 | Goffer |
| 2004/0023759 A1 | 2/2004 | Duncan et al. |
| 2006/0247095 A1 | 11/2006 | Rummerfield |
| 2007/0208392 A1 | 9/2007 | Kuschner et al. |
| 2010/0170546 A1 | 7/2010 | Popovic et al. |
| 2012/0000496 A1 | 1/2012 | Razon |
| 2014/0087922 A1 | 3/2014 | Bayerlein et al. |
| 2015/0075575 A1 | 3/2015 | Karlovich |
| 2015/0351995 A1 | 12/2015 | Zoss et al. |
| 2016/0166454 A1 | 6/2016 | Johnson et al. |
| 2016/0310731 A1* | 10/2016 | Dixon .................. A61H 1/024 |
| 2016/0331626 A1 | 11/2016 | Fellingham et al. |
| 2017/0281453 A1 | 10/2017 | Goldfarb et al. |
| 2018/0330817 A1 | 11/2018 | Avni et al. |
| 2019/0015273 A1 | 1/2019 | Linon |
| 2019/0046828 A1 | 2/2019 | Kuehne et al. |
| 2019/0060154 A1 | 2/2019 | Lee et al. |
| 2019/0099315 A1 | 4/2019 | Kuehne et al. |
| 2019/0183719 A1 | 6/2019 | Koscielski et al. |
| 2019/0216674 A1 | 7/2019 | Maggu et al. |
| 2019/0231632 A1 | 8/2019 | Hoekelmann et al. |
| 2019/0282431 A1 | 9/2019 | Moore |

FOREIGN PATENT DOCUMENTS

| | | |
|---|---|---|
| CA | 2232672 | 8/2001 |
| CN | 2203355129 U | 12/2013 |
| CN | 102580240 B | 1/2014 |
| CN | 104056353 A | 9/2014 |
| CN | 204233610 U | 4/2015 |
| CN | 106334265 | 1/2017 |
| DE | 60207069 T2 | 7/2006 |
| EP | 2907495 | 8/2015 |
| GB | 2484463 | 4/2012 |
| JP | 200431355 A | 11/2004 |
| JP | 6175050 B | 8/2017 |
| RU | 157028 | 11/2015 |
| WO | WO2006118756 | 9/2006 |
| WO | WO2014001853 | 3/2014 |
| WO | WO2014177206 | 11/2014 |

* cited by examiner

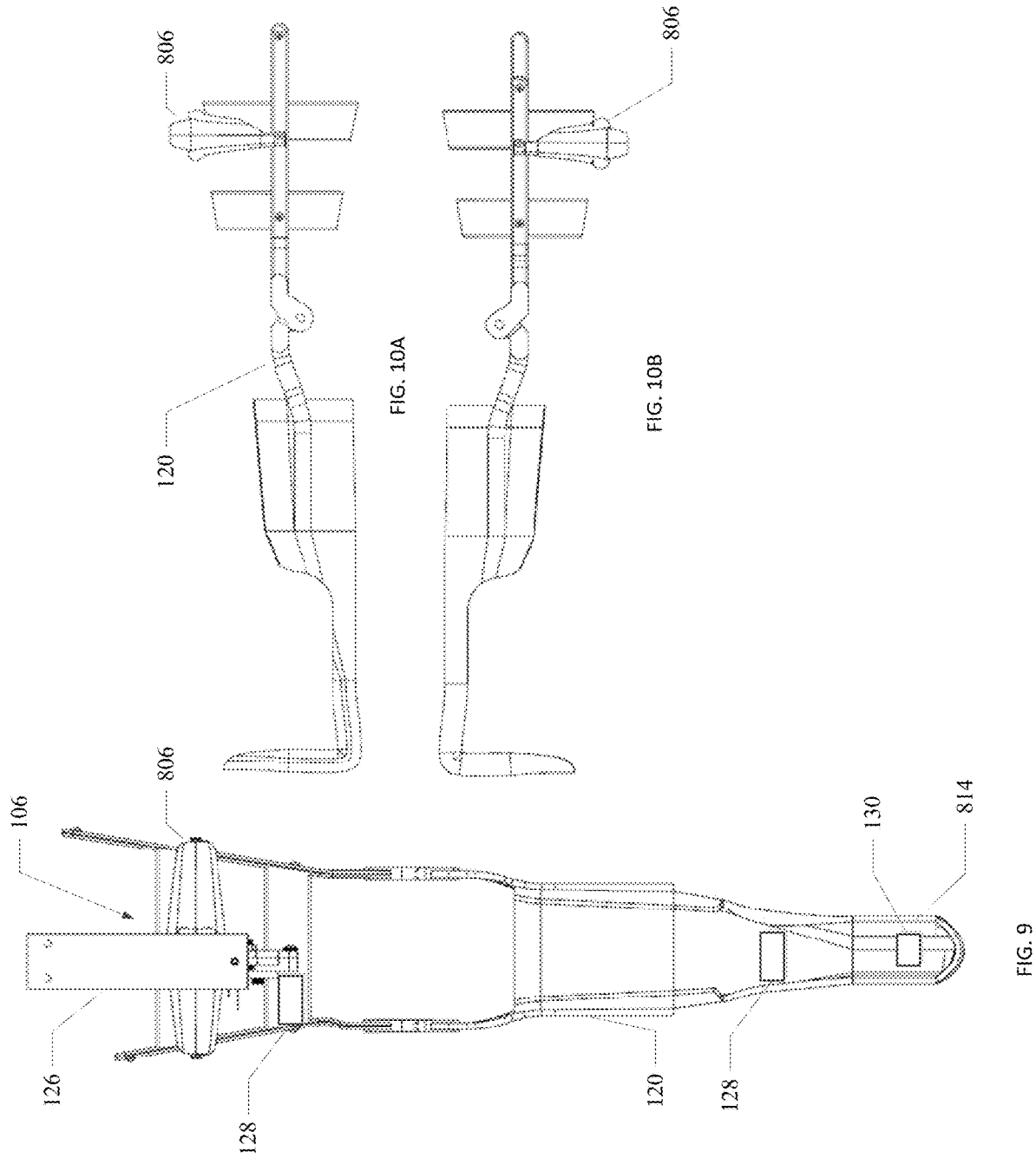

GAIT TRAINER WITH NEUROMODULATION INTEGRATION

CROSS REFERENCE TO RELATED APPLICATIONS

This application claims benefit of the filing date U.S. Provisional Patent Application No. 62/916,863 entitled Gait Trainer With Attached Brace Component and Neuromodulation Integration, filed on Oct. 18, 2019, which is herein incorporated by reference in its entirely.

BACKGROUND

A stroke is caused by a lack of blood flow to the brain. The blood flow is commonly prevented either by clotting which obstructs the blood flow or by ruptured blood vessels which prevent the flow. This lack of blood flow prevents the necessary oxygen to maintain brain cells. When these brain cells die, movements controlled by that area of the brain can be lost. The change caused by the death of these cells can vary due to many factors but more than two thirds of patients who suffer a stroke report having some type of disability.

Although there is a great variability in the severity and disability of a stroke, the uniform predictor for long-term recovery is early intervention and acute rehabilitation. However, the accepted clinical protocols and insurances only approve 16 days of inpatient rehabilitation for the most severe patients, leaving the remainder of patients to return home with adaptive equipment (wheelchair, crutches or a walker). Due to limited rehabilitation, patients do not experience facilitated, functional muscle activation, normal pelvic motion or coordinated locomotion and are vulnerable to enduring further physiological decline.

Current therapeutic techniques used with these patients are not versatile and are only temporarily effective. Using the currently practiced techniques, these patients are unable to maximize their neural recovery, rendering them unable to regain full functionality of their normal pelvic motion nor their full coordinated locomotion. These patients experience physiological decline and are often unable to return to their normal lives after experiencing their stroke. Current devices on the market targeted towards these patients either do not facilitate the return of a healthy gait pattern or cannot be used independently, resulting in a large barrier to the patient's recovery. While this problem is unfortunately common with stroke victims, it is also experienced by other individuals with neuro-deficits that endure the same barriers to recovery.

BRIEF SUMMARY

The following presents a simplified summary in order to provide a basic understanding of some aspects of the claimed subject matter. This summary is not an extensive overview. It is not intended to either identify key or critical elements or to delineate the scope of the claimed subject matter. Its sole purpose is to present some concepts in a simplified form as a prelude to the more detailed description that is presented later.

The described apparatuses and methods relate to medical and therapeutic devices and more particularly to gait training medical walkers for those with a compromised limb. While conventional gait training medical walkers assist in stabilization of the patient during their physical therapy to correct their maladapted gait, they are not well suited to provide muscle activation to the patient to facilitate gait correct.

The gait training device described herein, in aspects, gives a patient with a compromised limb mobility by providing a leg brace and medical walker attached through a flexible linkage which mechanically guides the limb through the biomechanics of walking, while utilizing neuromodulators to deliver electrical signals which activate the muscles in the compromised limb to facilitate correction of the patient's maladapted gait. In aspects, the described gait training device uses sensors to gather data on the position of the compromised limb in the gait cycle, allowing a neuromodulation controller to properly determine when it is most appropriate to deliver the electrical impulses to the compromised limb. The neuromodulation controller processes the data from the sensors, transmits the order to deliver electrical impulses to the neuromodulators, which then deliver the impulses to specific muscles in the patient's compromised limb to achieve a desired motion of the patient's limb.

In embodiments, the gait training device includes an unweighting mechanism designed to support and relieve the patient of at least a portion of their body weight. Relieving a user of a portion of their weight allows them to focus on the technical aspects of their gait while not having the entirety of their weight on a compromised limb, facilitating recovery. In embodiments, the sensors used to determine the position of the compromised limb in the gait cycle are pressure sensors that are located at the bottom of the patient's foot. In other embodiments, the sensors read the position of the compromised limb spatially. In embodiments, the sensors are tilt sensors placed at specific locations along the compromised limb to determine the position of the limb in the gait cycle.

In embodiments, the leg brace is customized to each user depending on the severity of their condition. In embodiments, the leg brace can be removed from the swing-linkage, allowing the medical walker to be used by multiple patients or multiple leg braces for a single patient. In embodiments, the gait training device is a wheeled frame adapted to move along a floor surface.

To accomplishment of the foregoing and related ends, certain illustrative aspects of the claimed subject matter are described herein in connection with the following description and the annexed drawings. These aspects are indicative of various ways in which the subject matter may be practiced, all of which are intended to be within the scope of the claimed subject matter. Other advantages and novel features may become apparent from the following detailed description when considered in conjunction with the drawings.

BRIEF DESCRIPTION OF THE DRAWINGS

The systems, devices and methods may be better understood by referring to the following description in conjunction with the accompanying drawings, in which like numerals indicate like structural elements and features in various figures. The components in the figures are not necessarily to scale, and simply illustrate the principles of the systems, devices and methods. The accompanying drawings illustrate only possible embodiments of the systems, devices and methods and are therefore not to be considered limiting in scope.

FIG. 9 depicts a front view of the embodiment of the detached brace component.

FIG. 10A depicts a right side view of the embodiment of the detached brace component.

FIG. 10B depicts a left side view of the detached brace component.

DETAILED DESCRIPTION

Figure 1:
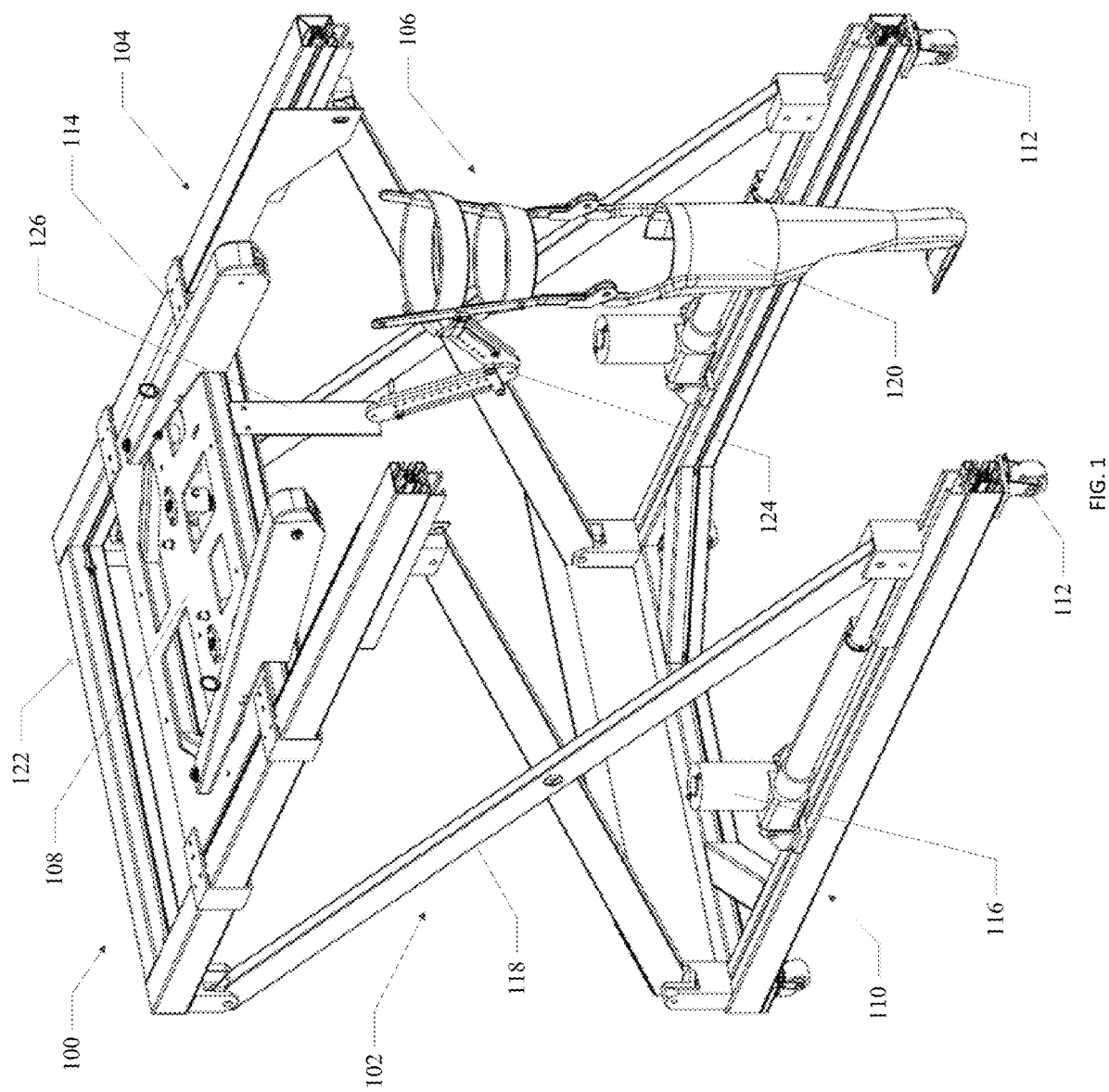
FIG. 1 depicts a perspective view of an embodiment of the gait trainer with attached brace component.
Figure 2:
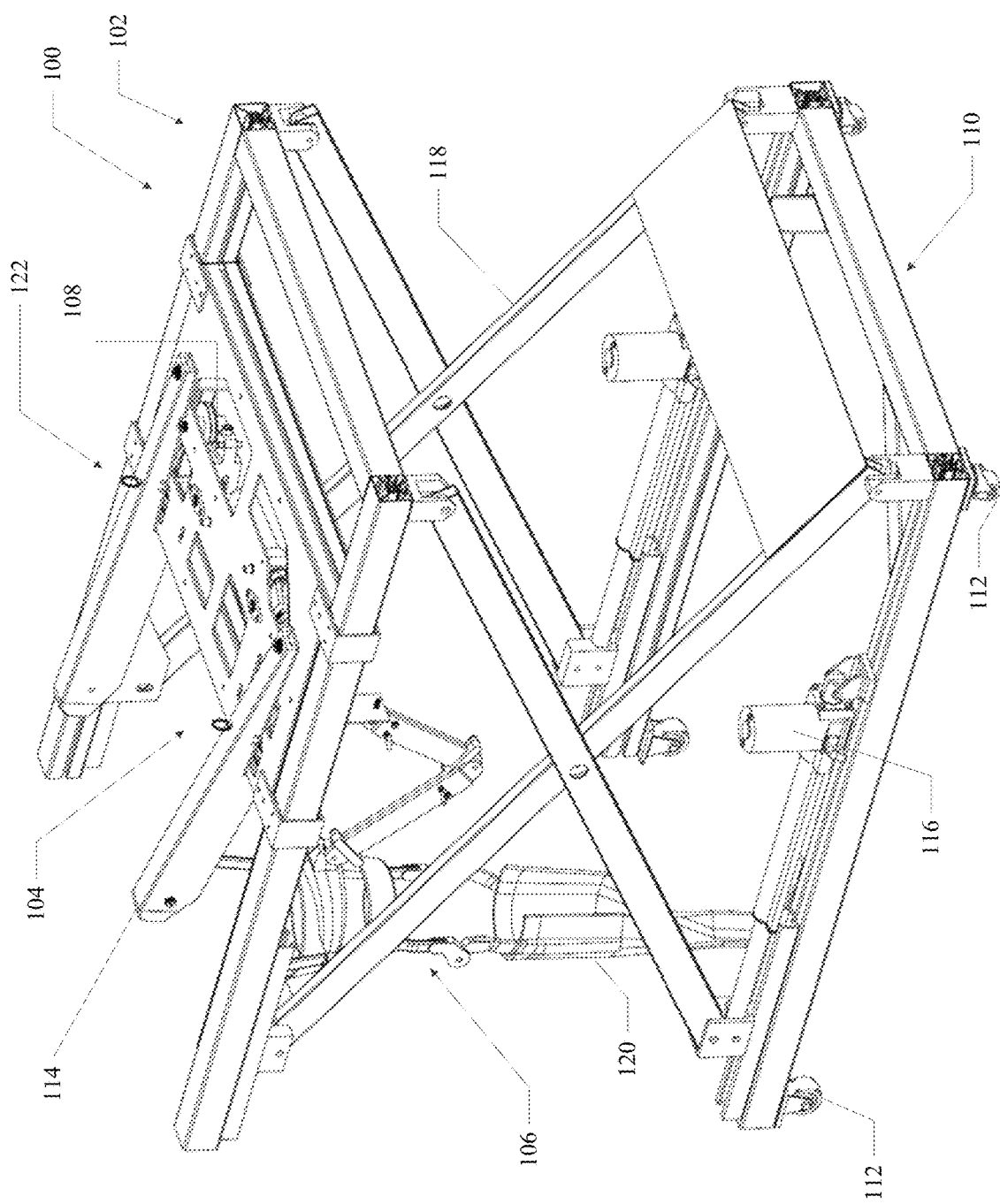
FIG. 2 depicts another perspective view of an embodiment of a gait trainer with attached brace component.
Figure 3:
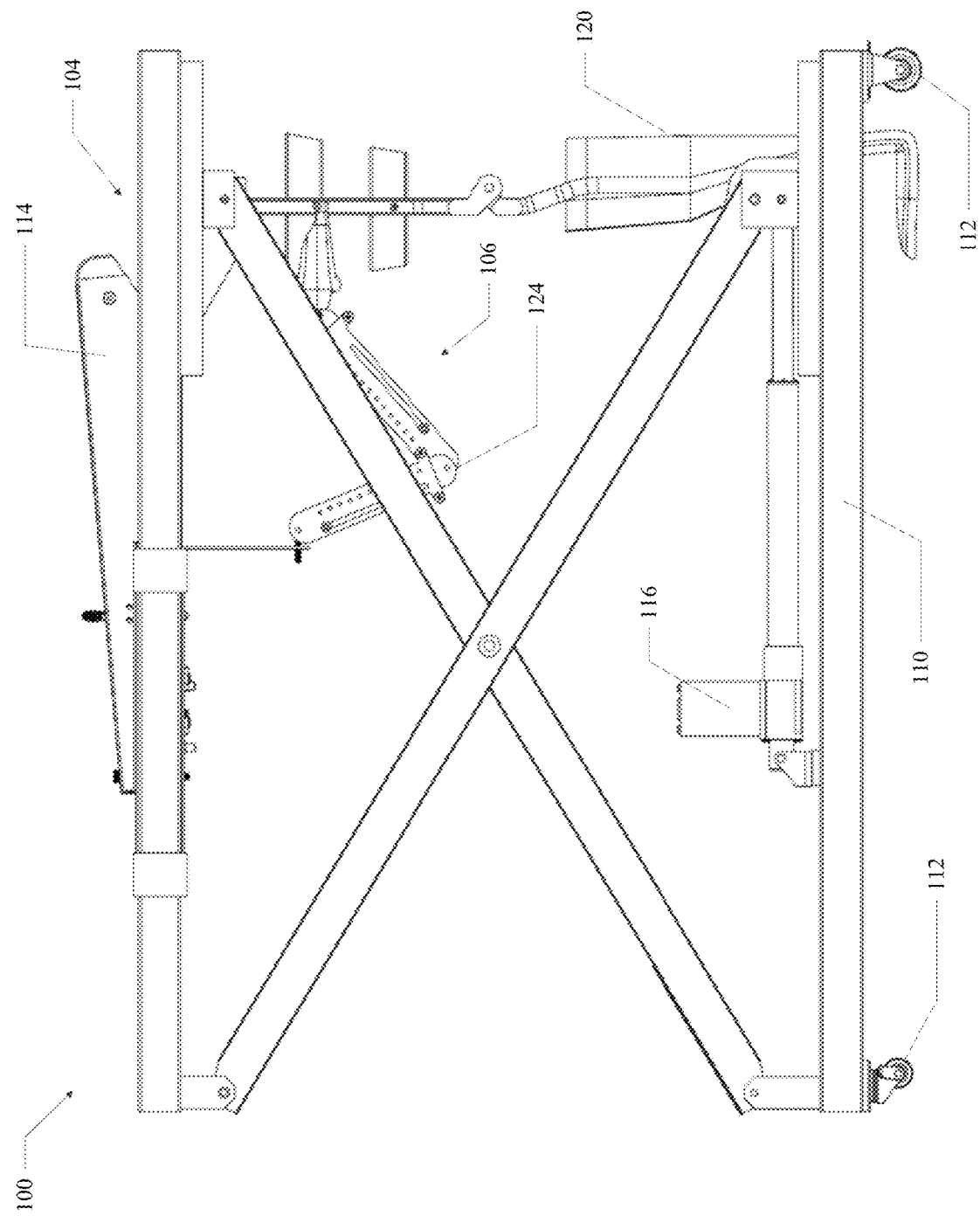
FIG. 3 depicts a side view of the embodiment of the gait trainer with attached brace component.
Figure 5:
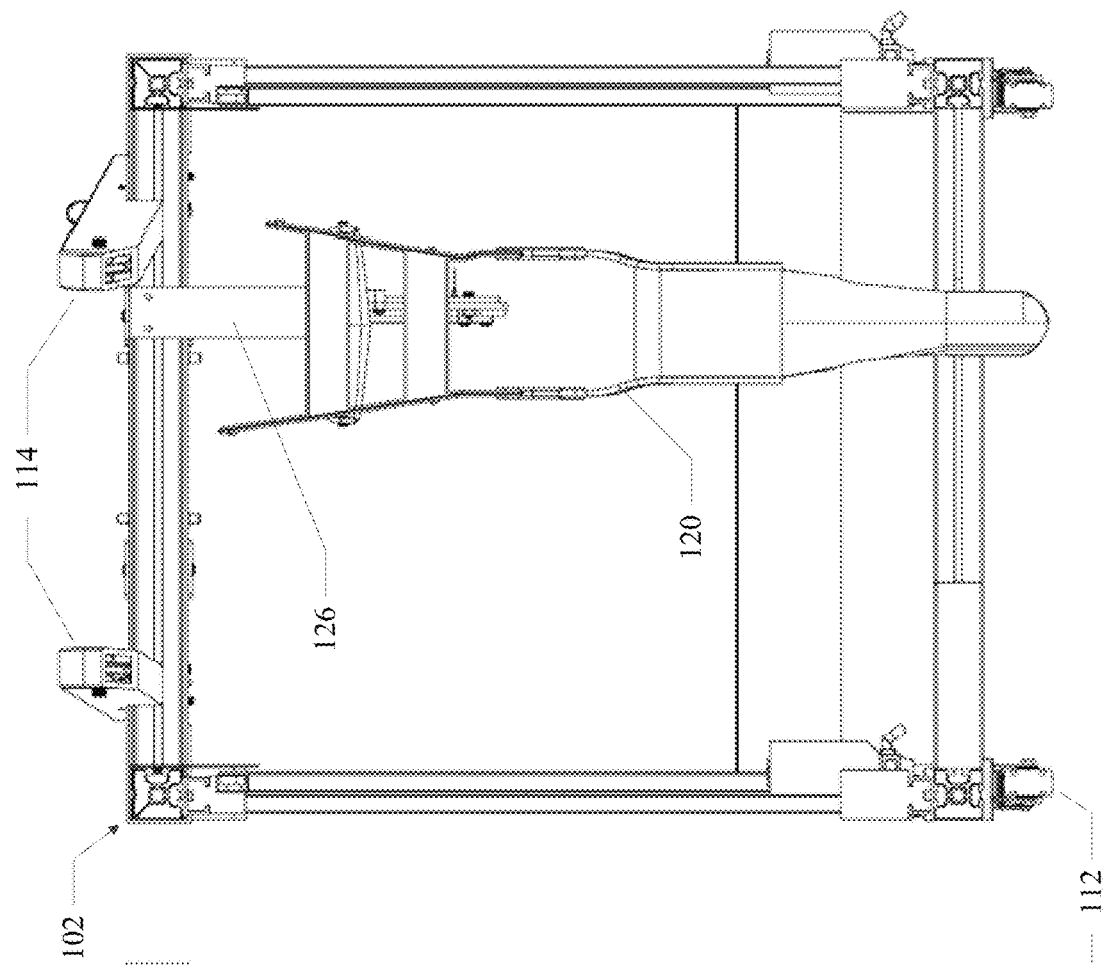
FIG. 5 depicts a rear view of the embodiment of the gait trainer with attached brace component.
Figure 4:
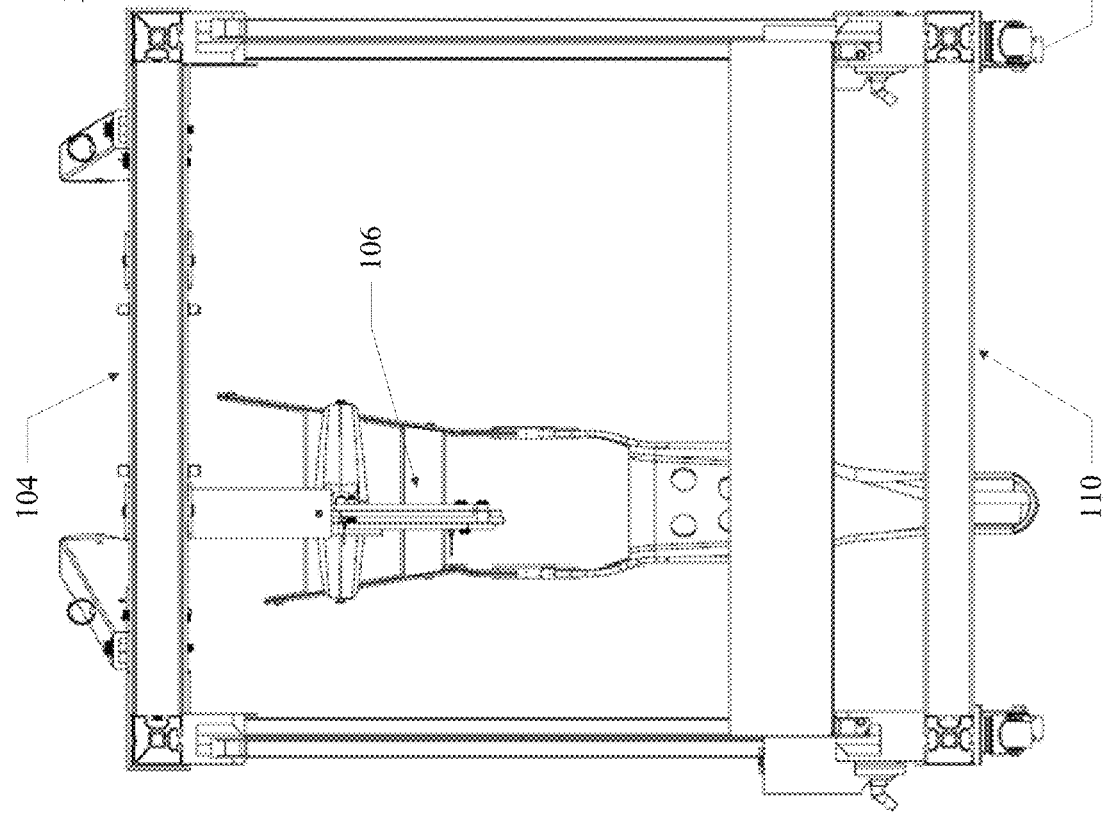
FIG. 4 depicts a front view of the embodiment of the gait trainer with attached brace component.
Figure 6:
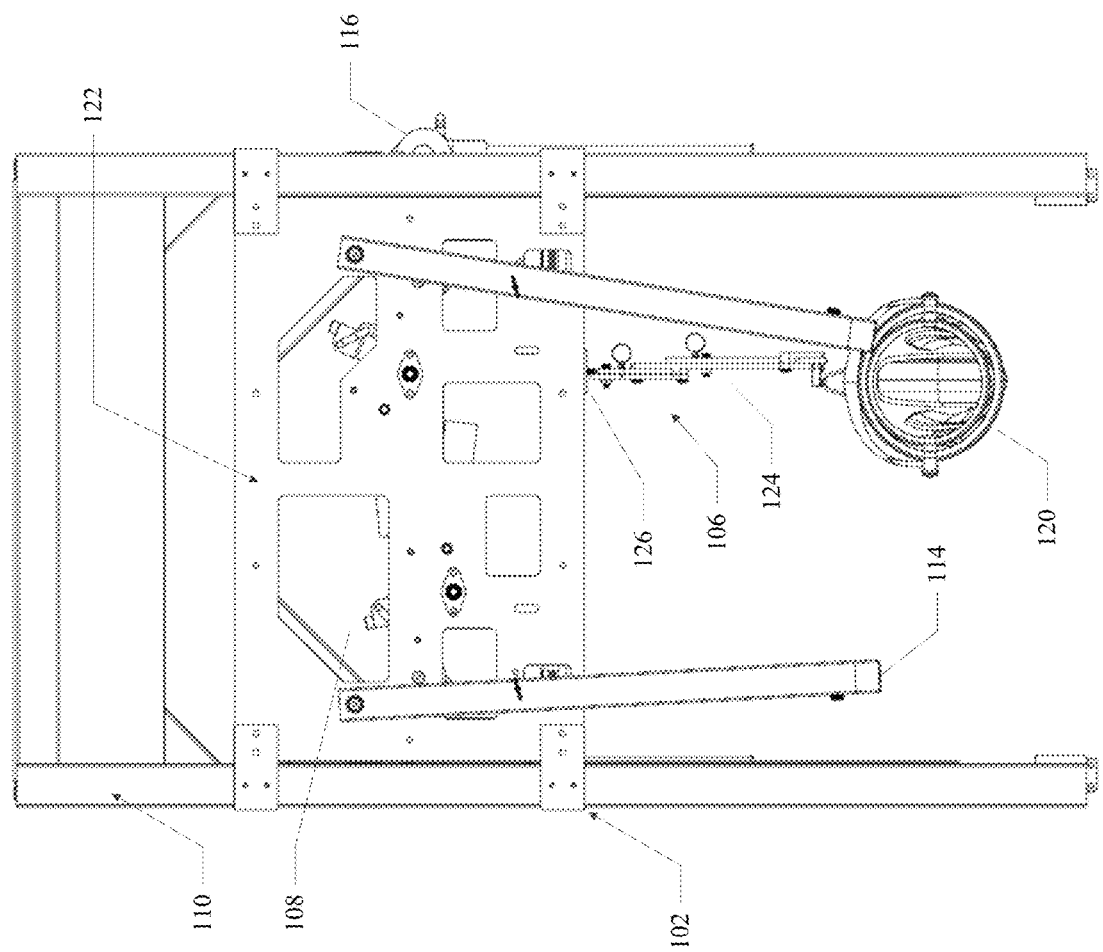
FIG. 6 depicts a top view of the embodiment of the gait trainer with attached brace component.
Figure 7:
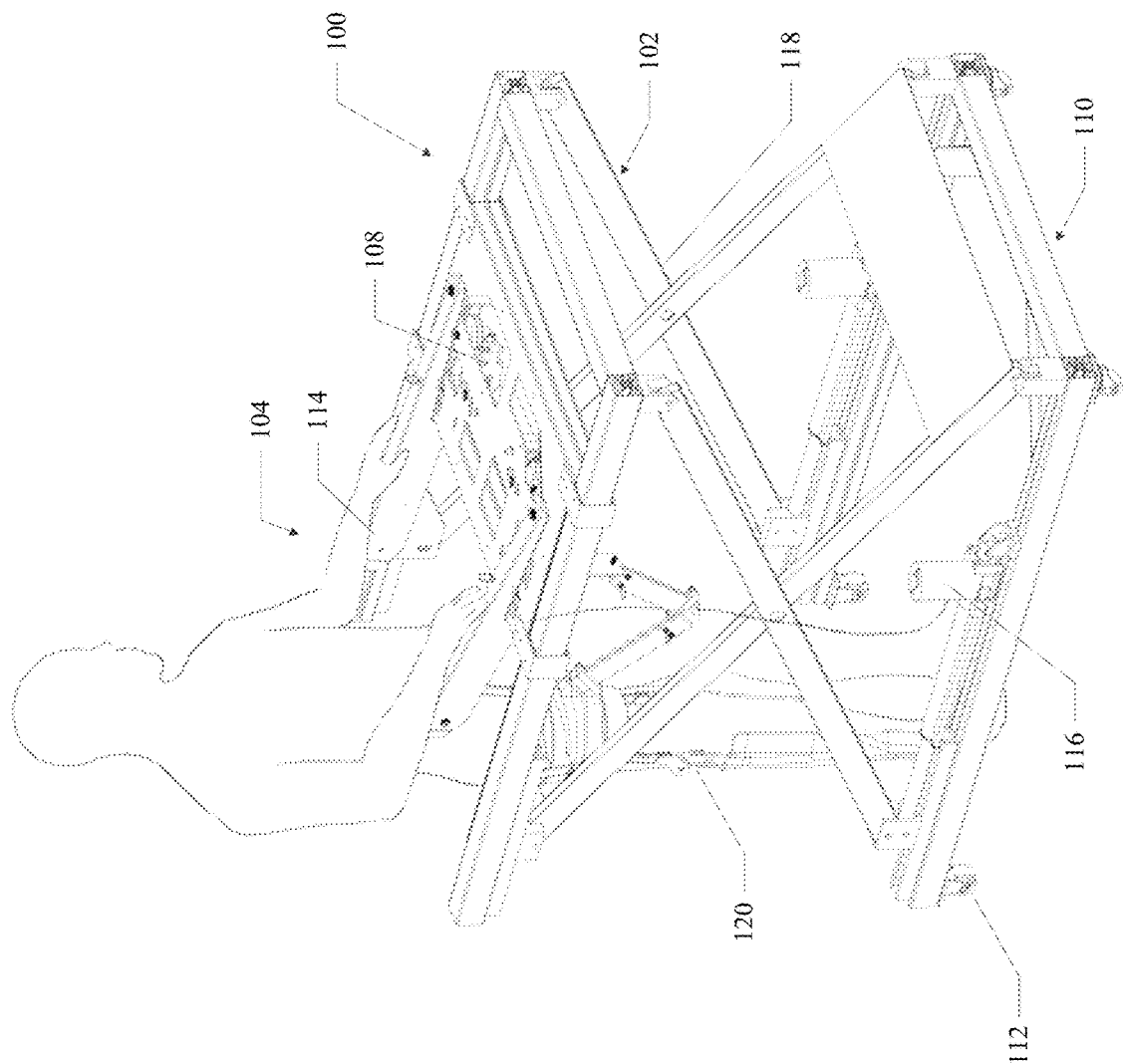
FIG. 7 depicts a perspective view of the embodiment of the gait trainer with attached brace component seen in FIG. 2 showing a user with an equipped leg brace connected to the medical walker.

Aspects of the system and methods are described below with reference to illustrative embodiments. The references to illustrative embodiments below are not made to limit the scope of the claimed subject matter. Instead, illustrative embodiments are used to aid in the description of various aspects of the systems and methods. The description, made by way of example and reference to illustrative reference is not meant to be limiting as regards any aspect of the claimed subject matter.

The described embodiments relate to medical and therapeutic devices and more particularly to gait training medical walkers for those with a compromised limb. In embodiments, the described gait training medical walker facilitates a normal gait motion for the compromised limb, allowing a user to correct their maladapted gait into a more natural gait. In embodiments, gait correction is achieved, at least in part, through the delivery of electrical pulses to specific muscles of the user, causing muscle contraction at deliberate points in time and through different, selected moments in the gait of the user. As used herein, the term walker includes any conventional walking assistance device including but not limited to rollators, wheeled walkers, or other mobility aids.

Carefully timed stimulus can contract selected muscles and assist the user in retraining their compromised limb. In embodiments, the gait training medical walker described herein can assist in retraining the muscles, enhancing the user's motor skills and eventually improving the user's mobility. Enhanced mobility has a huge impact on an individual's life. An incomplete recovery can cause people to limit their lives, avoiding uneven surface, or unfamiliar locations to reduce risks of falls.

A common problem in patients recovering from stroke is foot drop, where when the patient would normally swing their foot forward, the foot drops due to loss of dorsiflexion. This causes the patient to either drag their foot or try to fix the drag by lifting their knee higher, causing a "high step," which is characteristic of foot drop. Dragging the foot increases the likelihood that the patient will trip over an uneven surface, potentially injuring themselves. A high step is an unnatural motion that can cause its own issues with balance and negatively impact the patient's walking gait. Delivering a timed electrical impulse to the appropriate muscle or muscles of the patient will cause the muscle to contract, raising the foot as it swings forward.

Correcting gait can be critical for these patients. It enables them to walker faster, further, and with less effort than those with a maladapted gait. Additionally, having a maladapted gait can cause mental stress and insecurities for these patients, delaying or preventing recovery. Correcting gait will also decrease the risk of trips and falls, allowing the patient to resume more of their normal activities and participate in their community.

Neuromodulation is the alteration of nerve activity through targeted delivery of a stimulus. This alteration of nerve activity has been used to normalize nervous tissue function. While neuromodulation is utilized in a list of chronic conditions, it has also been used as an adjunctive treatment in recovery from a stroke. For example, one kind of neuromodulation, Functional Electrical Stimulation (FES) has been used to generate muscle contraction in limbs that are otherwise paralyzed. Using this application of neuromodulation, patients with paralyzed limbs could use an FES device to generate muscle contractions allowing functions such as grasping, walking, and standing. With respect to the foot drop example, neuromodulators would deliver the electrical impulses to the calf muscle. This would cause the patients calf muscle to contract, raising their foot.

The gait training medical walker described herein can provide improved rehabilitation and improved mobility by combining both support for the compromised limb, guidance in the motion of the limb, and integrated neuromodulation to activate the muscles of the compromised limb. The gait trainer improves the effectiveness of the neuromodulation by ensuring or assisting the muscle and limb to activate in a manner conducive to a normal gait by the user. The gait trainer reduces lateral movement in the limb, directing the movement to improve the natural gait and reduce potential problems from compensation for the compromised limb. This combination of guidance for the limb and assisted muscle activation can greatly enhance the recuperation and retraining of the compromised limb.

Referring to FIGS. 1-7, in an embodiment, a gait training medical walker 100 comprises a frame 102, upper body support 104, a limb gait system 106, an unweighting system 108, a leg brace 120, and a neuromodulation system. The frame 102 provides structural support and in the illustrated embodiment includes two cross bars aligned to be substantially parallel on either side of the user, which make up a support structure 118. In an embodiment, the support structure 118 is adjustable by the height adjustors 116, described in further detail below, allowing users of various height to adequately utilize the medical walker 100. The frame 102 is configured to support at least a portion of the weight of the user, allowing the user to use the frame 102 as a stabilizer while correcting their gait with the medical walker 100. In embodiments, the medical walker 100 comprises an upper body support 104. The upper body support can, in certain embodiments, include a set of forearm rests 114 which the user may place their arms upon as they move through their gait. Referring in particular to the embodiment in FIG. 7, a user can be seen utilizing the forearm rests 114 to maintain balance and to remove the necessity of putting their entire weight on a compromised limb. Referring back to the embodiments in FIGS. 1-6, the upper body support 104 is connected to the frame 102 to distribute the supported weight of the user. In embodiments, the unweighting system 108 aids in the support and distribution of weight off the user's compromised limb.

In the illustrated embodiments, the gait training medical walker 100 includes an unweighting system 108 shown attached to a portion of the upper body support 104. The unweighting system 108 permits the user to remove weight from the compromised limb while correcting their gait. In embodiments, the unweighting system 108 includes a harness, not shown, that attaches to the waist or mid-section of the user. The harness attaches to the unweighting system 108 and upper body support 104. A set of pulleys and springs can be used to selectively unweight the user and reduce stress on the compromised limb.

Figure 8:
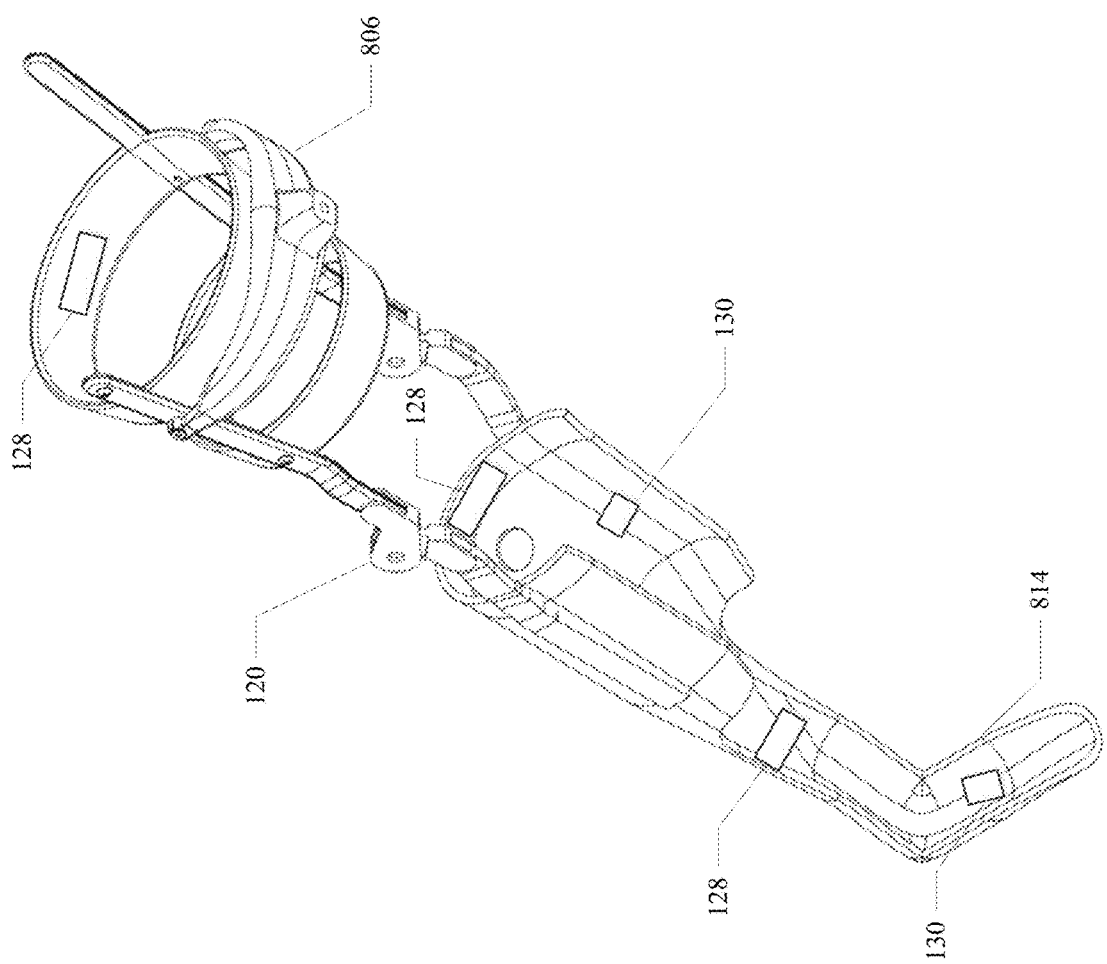
FIG. 8 depicts a perspective view of an embodiment of a detached brace component.

In embodiments, the gait training medical walker 100 includes an integrated neuromodulation system with a one or more neuromodulators 128 better shown in FIG. 8-9 that activate at least one muscle in the compromised limb of the user of the walker 100, and a neuromodulation controller 122 that signals the one or more neuromodulators 128 to deliver the electric impulses to the compromised limb. In an embodiment, the neuromodulation controller 122 delivers controls to the neuromodulators 128, where the neuromodulators 128 can be embedded in the leg brace 120. In another embodiment, the neuromodulators 128 are attached to the leg brace 106 and can be repositioned by a physical therapist as needed to enhance the therapy. In other embodiments, the neuromodulators 128 are fixed or embedded within the leg brace 106 ensuring consistent placement of the neuromodulators 128 with respect to the compromised limb. While in the illustrated embodiments, the neuromodulation controller 122 is located in the upper body support 104, it can be located elsewhere on the medical walker 100, on the leg brace 106 or nearby in alternative embodiments and the location is not essential to the delivery of controls to the neuromodulators, as long as the neuromodulation controller 122 is in communication with the neuromodulators 128. In embodiments, communication between the neuromodulation controller 122 and the neuromodulators 128 can be wired or wireless.

In embodiments, the frame 102 includes a base 110 with a plurality of connected bars resting on a plurality of wheels 112 that facilitate movement of the medical walker 100. In the illustrated embodiments, the height adjustors 116 rest atop the connected bars that make up the base 110, but the height adjustors 116 are not required to rest on the base 110. In embodiments, the height adjustors 116 are actuators which facilitate the movement of the support structure 118. The height adjustors 116 can pull at least one of the cross bars of the support structure 118 inward, raising the height of the upper body support 104, or can push the cross bar out, lowering the upper body support 104.

In embodiments, a limb gait system 106 is connected to the medical walker 100 by a gait system connector 126. In the shown embodiment, the gait system connector 126 is fastened to the medical walker 100 at one end and provides a stable connection point for the limb gait system 106. In an embodiment, the gait system connector 126 is height adjustable to allow customization for the dimensions of the user. The limb gait system 106 mechanically guides the user's compromised limb through a desired motion. At the opposite end of the limb gait system 106 is the leg brace 120. In embodiments, the size and shape of leg brace 120 will vary depending on the pathology and severity of the user's compromised limb. The swing linkage 124 connects the leg brace 120 and the gait system connector 126.

In the illustrated embodiments, the swing linkage 124 allows customization based on the user to best accommodate the desired gait correction through mechanically guiding the user. In embodiments, the swing linkage includes one or more arms connected via a hinge joint. The arms can be adjustable in length to suit the length of stride of the user and prevent drag of the compromised limb. In embodiments, the length of the arms can limit the rearward motion of the swing linkage 124 and therefore the compromised limb. This encourages the user to stride with the compromised limb and discourages dragging of the limb. By stopping the rearward motion of the swing linkage 124, the gait trainer communicates to the user when the gait motion has completed for a particular step and when it is time to begin another step and continue the gait motion. In another embodiment, the swing linkage 124 can include a hard stop implemented as a simple bar that limits the rotation of the arm relative to the gait system connector 126, thereby limiting the rearward motion of the swing linkage 124.

Additionally, in embodiments, the swing linkage 124 is adjustable to accommodate different heights of the user or to vary the location of attachment to the leg brace 120. In embodiments, the limb gait system 106 is designed to allow movement of the user's compromised limb in a selected plane of motion but restrict movement in other planes of motion. In those embodiments, this can facilitate correction of gait by mechanically guiding the user to move the compromised limb backward and forward, while preventing or limiting lateral motion of the limb. In some cases, users with maladapted gait will attempt to correct their stride without using the compromised limb. This change in stride can create a gait that puts stress on other muscles or joints. Additionally, this adjustment can lead to a gait that has a higher likelihood of falls or trips. In these embodiments, the swing linkage 106 restricts the movement of the user such that they are unable to rely on these unhealthy corrections and must utilize the compromised limb to correct their gait. Of course, this is made easier by embodiments containing the upper body support 104, forearm rests 114, and/or the unweighting system 108. In these embodiments, the user is able to work on their gait correction without putting their full body weight on the compromised limb and, through the aid of a physical therapist or other professional, regain muscle in this limb, facilitating recovery of their natural gait.

In embodiments the swing linkage 124 connects to the leg brace 120 proximate to the knee or below the hip. By connecting proximate to the knee, and below the hip of the user, the gait training walker 100 can guide the movement of the compromised limb, but does not need to be customized to fit the waist or hip dimensions of the user.

Turning now to FIGS. 8 and 9, in embodiments, embedded within the leg brace 120 are neuromodulators 128. The neuromodulators 128 deliver electrical impulses to specific muscles of the user to force that muscle to contract. In embodiments, the neuromodulators 128 are custom placed in or on the leg brace 120 depending on the user and desired gait corrections. The forced contractions of the user's muscles work to correct the maladaptive gait of the user. In certain embodiments there are spatial sensors 130 attached to the frame 102 or leg brace 120 which detect movement of the user's compromised limb in space. In alternative embodiments, the sensors 130 are pressure sensors attached to the foot portion 814 of the leg brace 120. In other alternative embodiments, the sensors 130 are tilt sensors, which are attached to leg brace 120 and detect axis tilt. Irrespective of which type of sensors are utilized, the sensors 130 detect data related to the position and motion of the user's leg. This data can be used to correct the user's gait via analysis by the neuromodulation controller 122 and signals to the neuromodulators 128.

Referring now to the embodiments illustrated in FIGS. 8-10, the leg brace 120 can include a foot portion 814 and is attached to a yoke 806. The foot portion 814 can serve a way to better attach the leg brace 120 securely on the compromised limb of the patient. Additionally, in certain embodiments, the foot portion 814 can be an effective location for pressure sensors 130. The pressure sensors 130 gather data used by the neuromodulation controller 122. The yoke 806 connects the leg brace 120 to the swing linkage 124 and permits slight deviation from planar motion of the compromised limb, while still limiting abduction and adduction. In embodiments, the leg brace 120 serves as both support for the patient's compromised limb, allowing the patient to gradually put more weight on the compromised limb, as well as serving as a location for neuromodulators 128 and possibly sensors 130. In embodiments, the leg brace 120 will be customized depending on the patient and their stage of recovery.

In the illustrated embodiments, the leg brace 120 can be customized to receive the compromised limb of the patient. In certain embodiments, the leg brace 120 fits snugly around the compromised limb and connects, through the yoke 806, to the swing linkage at the upper thigh area of the compromise limb. If connected higher up the leg of the user, the connection facilitates use of the leg brace 120 by amputees, reducing the pressure put upon the amputation wound.

While the leg brace 120 can be made from differing material depending on the needs of the user, the illustrated embodiment has rigidity that maintain the stability and provide support for the compromised limb. The additional support from this embodiment reduces the stress put upon the compromised limb, facilitating focus on gait correction by the user.

Figure 11:
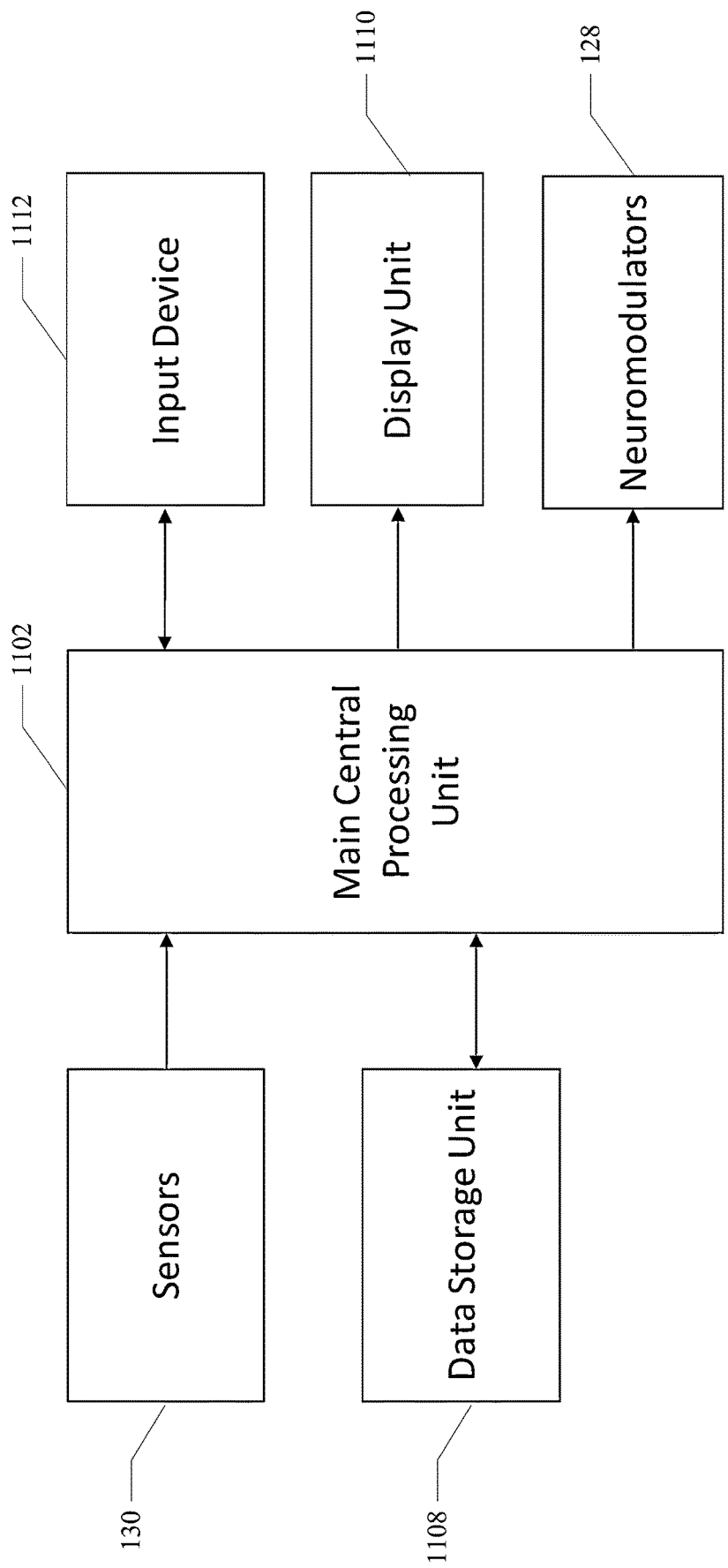
FIG. 11 depicts an embodiment's block diagram overview of the neuromodulation system.

FIG. 11 is a block diagram of the neuromodulation system including a neuromodulator controller 122 to control the neuromodulators 128 to deliver adequate electrical impulses at the appropriate times. The neuromodulator controller 122 includes a main central processing unit 1102, referred herein as "CPU" or "processing unit," and is connected to sensors 130, neuromodulators 128. The neuromodulator controller 122 can include a data storage unit 1108, a display unit 1110, and an input device 1112.

The sensors 130 gather data on the compromised limb of the user. In embodiments, these sensors 130 spatially detect the motion or location of the compromised limb. In alternative embodiments, these sensors 130 are configured to detect pressure at the foot of the user. In other alternative embodiments, these sensors 130 detect the tilt of the compromised limb to determine where in the gait motion the compromised limb is currently located. In other embodiments, there are a plurality of types sensors 130 that provide data to the neuromodulator controller 122. The sensors 130 provide the CPU 1102 sufficient data to adequately detect the compromised limb motion and position of the compromised limb is in the gait motion. In certain embodiments, the data is stored in a data storage unit 1108. The CPU 1102 processes the gait information obtained by the sensors 130 and stored in the data storage unit 1108 to determine the muscles that require force contraction, or the neuromodulators 128 to signal to correct the user's gait. In alternative embodiments, a physical therapist or other professional will input the corrections into the CPU 1102 manually, through the input device 1112. In certain embodiments, the input device 1112 is also the display unit 1110, such as with touch screen devices.

While the user proceeds with their walking motion, the CPU 1102 detects the motion or gait cycle of the compromised limb through the sensors 130. The CPU 1102 will signal one or more of the neuromodulators 128 to deliver an electrical impulse to a muscle at a specified time in the gait cycle, resulting in correction of the user's maladapted gait.

Figure 12:
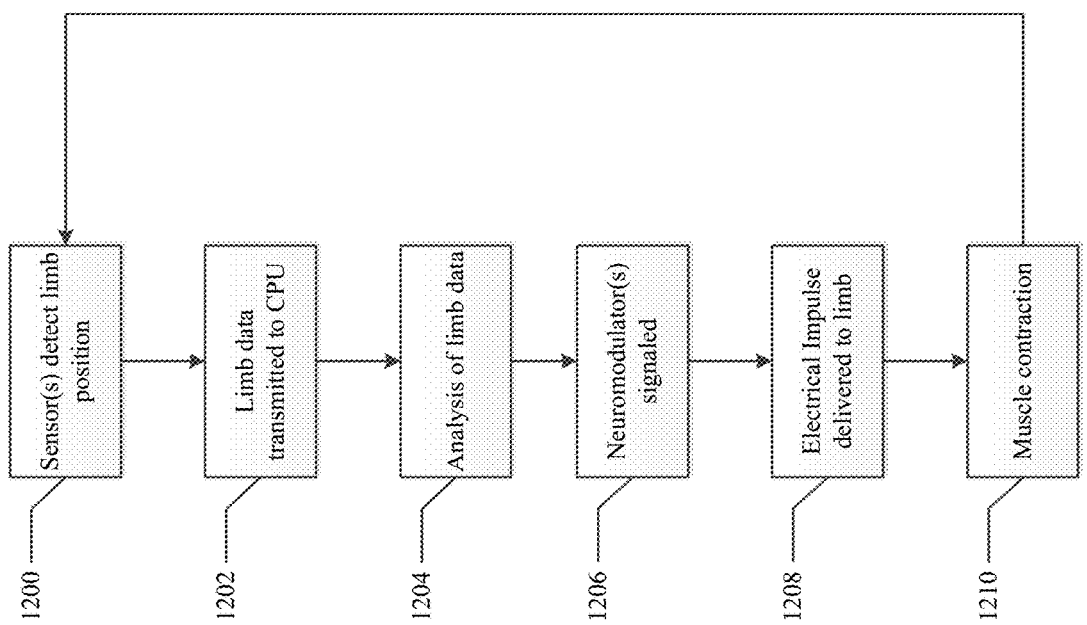
FIG. 12 is a flowchart depicting a method of gait training with integrated neuromodulation.

Turning now to FIG. 12, a method for gait training using integrated neuromodulation is illustrated. At step 1200, one or more sensors 130 detect position and or motion of the compromised limb and transmit the position and motion data to the CPU 1102 of the neuromodulator controller 122 at step 1202. The received data can be retained in the data storage unit 1108, and at step 1204 the CPU 1102 can analyze the data and calculate the timing for triggering the neuromodulators 128. At the appropriate time, at step 1206, the CPU 1102 signals the neuromodulators 128 causing the neuromodulators 128 to deliver an electrical impulse to the user's limb at step 1208. This impulse causes the muscle to contract assisting proper gait of the user at step 12010. In embodiments, at step 1200, the sensors 130 collect data on the limb position and motion during the correction by the neuromodulators 128 and that data can be used by the CPU 1102 to evaluate the timing of the signal to the neuromodulators 128 for future corrections.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has" or "having" or variations in form thereof are used in either the detailed description or the claims, such terms are intended to be inclusive in a manner similar to the term "comprising" as "comprising" is interpreted when employed as a transitional word in a claim.

What is claimed is:

1. A gait training device, comprising:
    a medical walker;
    a leg brace operably connected to the medical walker;
    a swing-linkage which physically connects the leg brace to the medical walker, and limits abduction and adduction of the user's limb;
    one or more sensors that detect movement of a user's limb;
    one or more neuromodulators attached to the leg brace, the neuromodulators positioned to deliver electrical impulses to the user's limb; and
    a neuromodulation controller that processes data from the sensors and transmits signals to the neuromodulators to direct the neuromodulators to deliver the electrical impulses, wherein the electrical impulses cause a specific muscle to contract to accomplish a desired motion of the user's limb.

2. The gait training device of claim 1, further comprising an unweighting mechanism that relieves a user of at least a portion of their body weight.

3. The gait training device of claim 1, wherein the sensors are configured to detect pressure at the bottom of the user's foot.

4. The gait training device of claim 1, wherein the leg brace is removable from the swing linkage.

5. The gait training device of claim 1, wherein the neuromodulators are embedded in the leg brace and customized to be specific to the pathology and severity of the condition of a user.

6. The gait training device of claim 1, wherein the sensors are configured to detect the position of the leg brace in space.

7. The gait training device of claim 6, wherein the swing linkage is attached to the leg brace proximate to a knee of the user's limb.

8. The gait training device of claim 1, wherein the medical walker is a moveable frame and the user is operably connected to the moveable frame through the limb brace.

9. The gait training device of claim 1, wherein at least one of the plurality of sensors is a tilt sensor configured to detect motion of the user's limb.

* * * * *